(12) United States Patent
Dashevsky et al.

(10) Patent No.: US 8,461,843 B2
(45) Date of Patent: Jun. 11, 2013

(54) METHOD AND SYSTEM FOR MEASURING RESISTIVITY ANISOTROPY OF LAYERED ROCK SAMPLES

(75) Inventors: Yuliy A. Dashevsky, Novosibirsk (RU); Sergey A. Terentev, Omsk (RU)

(73) Assignee: Baker Hughes Incorporated, Houston, TX (US)

( * ) Notice: Subject to any disclaimer, the term of this patent is extended or adjusted under 35 U.S.C. 154(b) by 622 days.

(21) Appl. No.: 12/687,917

(22) Filed: Jan. 15, 2010

(65) Prior Publication Data

US 2011/0037474 A1 Feb. 17, 2011

Related U.S. Application Data

(63) Continuation of application No. PCT/RU2009/000400, filed on Aug. 12, 2009.

(51) Int. Cl.
*G01V 3/00* (2006.01)

(52) U.S. Cl.
USPC .......................................... 324/376

(58) Field of Classification Search
USPC .......................................... 324/376
See application file for complete search history.

(56) References Cited

U.S. PATENT DOCUMENTS

| | | | | |
|---|---|---|---|---|
| 2,613,250 A | * | 10/1952 | Dunlap et al. | 324/693 |
| 2,802,173 A | * | 8/1957 | Nisle | 324/376 |
| 4,686,477 A | * | 8/1987 | Givens et al. | 324/366 |
| 5,503,001 A | * | 4/1996 | Wong | 73/38 |
| 7,221,165 B2 | | 5/2007 | Fleury | |
| 2004/0133351 A1 | * | 7/2004 | Frenkel et al. | 702/7 |

FOREIGN PATENT DOCUMENTS

GB 2243690 A * 11/1991

OTHER PUBLICATIONS

Hagiwara, T. 1996. EM Log Response to Anisotropic Resistivity in Thinly Laminated Formations with Emphasis on 2-MHz Resistivity Devices. Paper 28426-PA SPE FE. 11 (4): 211-217.
Klein J. D. 1991. Induction Log Anisotropy Corrections. Paper T, presented at SPWLA 32nd Annual Logging Symposium, Jun. 16-19.
Zhdanov, M. S., Kennedy W. D., Cheryauka A. A. and Peksen, E. 2001. Principles of Tensor Induction Well Logging in Deviated Well in and Anisotropic Environment. Paper R. presented at SPWLA 42nd Annual Logging Symposium, Jun. 17-20.
Hagiwara, T. 1995. Anisotrpoic Shale and Induction Log Shoulder Bed Corrections for Deviated Boreholes. Paper Z, presented at SPWLA 36th Annual Logging Symposium, Jun. 26-29.
Moran, J. H., and Gianzero, S., 1979. Effects of Formation Anisotropy on Resistivity-logging Measurements, Geophysics, 44 (7): 1266-1286.

(Continued)

*Primary Examiner* — Jay Patidar
(74) *Attorney, Agent, or Firm* — Cantor Colburn LLP

(57) ABSTRACT

A method and apparatus for measuring the resistivity anisotropy of cylindrical rock samples is disclosed. The measurement setup includes two pairs of electrodes that contact the sample surface. The ring electrodes of the first pair are disposed on the cylindrical surface of the sample. The cap electrodes of the second pair are mounted at the sample ends. Two differences in potentials are measured. One of the cap electrodes and the nearest ring electrode are used to measure the first difference that results from current injected through the remaining cap and ring electrodes. The second difference is measured between the two ring electrodes, while current is injected through the first and second end cap electrodes. These two differences are inverted for the anisotropy coefficient, horizontal and vertical resistivity.

7 Claims, 11 Drawing Sheets

OTHER PUBLICATIONS

Kunz, K. S., and Moran J. H., 1958. Some Effects of Formation Anisotropy on Resistivity Measurements in Boreholes. Geophysics, 23 (4): 770-194.

Sclumberger, C., Sclumberger, M. and Leonardon, E. G. 1934. Some Observations concerning electrical measurements in anisotropic media and their interpretations: Transactions of American Institute of Mining Engineers, 110: p. 159.

* cited by examiner

METHOD AND SYSTEM FOR MEASURING RESISTIVITY ANISOTROPY OF LAYERED ROCK SAMPLES

FIELD OF THE INVENTION

The present invention disclosure relates to the analysis of rock samples, and more particularly relates to the measurement of resistivity anisotropy (horizontal and vertical resistivity) of rock samples exhibiting layerings such as laminations.

BACKGROUND OF THE INVENTION

In conventional logging systems used in the exploration and production of hydrocarbons from subterranean formations, the distances between the electrodes or antennas are usually great enough that the rock volume involved in a measurement may include several thin beds having different lithological characteristics and, therefore different resistivity. Such layering can arise from the existence of clay layers or from compacted sand beds of differing grain sizes.

When individual layers are not resolved by a logging tool, the tool responds to the formation as if it were a macroscopically anisotropic formation. It holds true for thinly laminated sand/shale sequences.

If a rock sample is cut from the anisotropic formation, the resistivity of the sample measured with current flowing parallel to the bedding plane is called the transversal or horizontal resistivity. The resistivity measured with the current flowing perpendicular to the bedding plane is called the longitudinal or vertical resistivity.

One of the generally accepted approaches to measure the resistivity anisotropy of layered rock sample consists of following steps. A cube is cut from the layered rock sample. Then measurement of the resistivity of the cube in the three orthogonal directions is performed. The two resistivities measured for current flow parallel to bedding are longitudinal resistivities, $\rho_l$ and they should be fairly similar. The resistivity measured with current across bedding is the transverse resistivity, $\rho_n$. The ratio $\Lambda = \sqrt{\rho_n/\rho_l}$ is called the coefficient of anisotropy.

Typically, a core sample is cylindrical with flat end faces. Both two- and four-electrode measurement configurations are known which allow the effective determination of resistivity of isotropic core samples.

In the two-electrode case current is injected through two cap electrodes at the ends. With two-electrode design the current and potential electrodes are combined. The rock-electrode couplings constitute the principal disadvantages of two-electrode measurements, if badly designed. The contact resistance decreases with increasing pressure, so the contacts must be put under enough pressure to make the contact resistance a small fraction of the rock resistance.

Advantages of two-electrode arrays include the resistivity measurement of entire sample. This is considered desirable, since the porosity and water saturation are also generally measured on the entire sample.

In the four-electrode case, current is similarly injected through two cap electrodes at the ends. However, a four-electrode arrangement incorporates two additional ring electrodes. These measuring electrodes (metal rings) are placed along the core length. The advantage of the four-electrode setup is that it is not sensitive to the contact resistance. A disadvantage, however, is that the voltage is measured over a shorter distance and the result can be sensitive to small inhomogeneities in the core.

Both two- and four-electrode measurement configurations have a similar dominant characteristic: they are symmetric relative to the major axis of the cylindrical core sample. Neither arrangement has heretofore been shown to be effective in resistivity measurements on anisotropic samples.

SUMMARY OF THE INVENTION

In view of the foregoing, the present invention involves the use of a four-electrode configuration for estimating the coefficient of anisotropy of a cylindrical rock sample and horizontal/vertical resistivity.

In accordance with one aspect of the invention, a method and apparatus for measuring the resistivity anisotropy of cylindrical rock samples exhibiting layering of different conductivities such as laminations is disclosed. In one embodiment, the method comprises setting a sample into a measurement setup that includes two pairs of electrodes contacting the sample surface. The ring electrodes of the first pair are spaced apart and disposed on the cylindrical surface of the sample. The cap electrodes of the second pair are at the sample ends. Two differences in potentials are measured. The two ring electrodes are used to measure the first difference. In this case a current between the pair of cap electrodes is used to drive the current. The second difference is measured between one of the cap electrodes and the nearest ring electrode, and the current is driven between the remaining cap electrode and the ring electrodes. These two differences are inverted for the resistivity anisotropy that comprises vertical and horizontal resistivity. The terms horizontal and vertical are defined to be those parallel to and perpendicular to the bedding plane, respectively.

BRIEF DESCRIPTION OF THE DRAWINGS

The present invention is best understood with reference to the following detailed description of embodiments of the invention when read in conjunction with the attached drawings, in which like numerals refer to like elements, and in which.

DETAILED DESCRIPTION OF A PREFERRED EMBODIMENT OF THE INVENTION

In the disclosure that follows, in the interest of clarity, not all features of actual implementations are described. It will of course be appreciated that in the development of any such actual implementation, as in any such project, numerous engineering and technical decisions must be made to achieve the developers' specific goals and subgoals (e.g., compliance with system and technical constraints), which will vary from one implementation to another. Moreover, attention will necessarily be paid to proper engineering and programming practices for the environment in question. It will be appreciated that such development efforts might be complex and time-consuming, outside the knowledge base of typical laymen, but would nevertheless be a routine undertaking for those of ordinary skill in the relevant fields.

To facilitate an understanding of the present invention, it is first useful to consider the modeling of a formation of thickness H. For the purposes of modeling, it is assumed that the formation consists of parallel layering of sand and shale with the respective conductivities $\sigma_{sn}$, $\sigma_{sh}$ and thicknesses $h_{sn}$, $h_{sh}$. The total thicknesses of sand and shale are $H_{sn}$ and $H_{sh}$ respectively. In that case, $\Delta h_{sh}$ is an expression for the relative thickness of shale, where $\Delta h_{sh} = H_{sh}/H$.

Under the assumptions $H \gg h_{sh}$, $H \gg h_{sn}$, the layered formation can be treated as a uniform anisotropic medium with macroscopic conductivities $\sigma_t$, $\sigma_n$ and anisotropy coefficient $\Lambda = \sqrt{\sigma_t/\sigma_n}$, where:

$$\sigma_t = \sigma_{sn}\left(1 - \Delta h_{sh} + \Delta h_{sh}\frac{\sigma_{sh}}{\sigma_{sn}}\right),\tag{1}$$

$$\sigma_n = \frac{\sigma_{sn}}{1 - \Delta h_{sh} + \Delta h_{sh}\frac{\sigma_{sn}}{\sigma_{sh}}},$$

$$\Lambda = \left[\left(1 - \Delta h_{sh} + \Delta h_{sh}\frac{\sigma_{sh}}{\sigma_{sn}}\right)\left(1 - \Delta h_{sh} + \Delta h_{sh}\frac{\sigma_{sn}}{\sigma_{sh}}\right)\right]^{\frac{1}{2}}.$$

Parameters $\sigma_t$, $\sigma_n$ denote horizontal and vertical conductivity respectively.

Expressions (1) demonstrate that parameters $\sigma_{sn}$, $\sigma_{sh}$ can be estimated provided that $\sigma_t$, $\sigma_n$ and $\Delta h_{sh}$ are given.

In accordance with one aspect of the invention, certain signals are measured and the results of these measurements are then inverted for macroscopic parameters $\sigma_t$, $\sigma_n$, $\Lambda$ As far as the evaluation of parameter $\Delta h_{sh}$ is concerned, those of ordinary skill will appreciate that additional laboratory-based core analysis is required, for example, digital photography, X-ray tomography of full-size core samples, etc.

For example, X-ray tomography of core sample allows evaluating thickness of laminations, volumes, geometric parameters, etc. Resolution capabilities are ~0.2% by contrast, ~0.4 mm in 3D.

Figure 1:
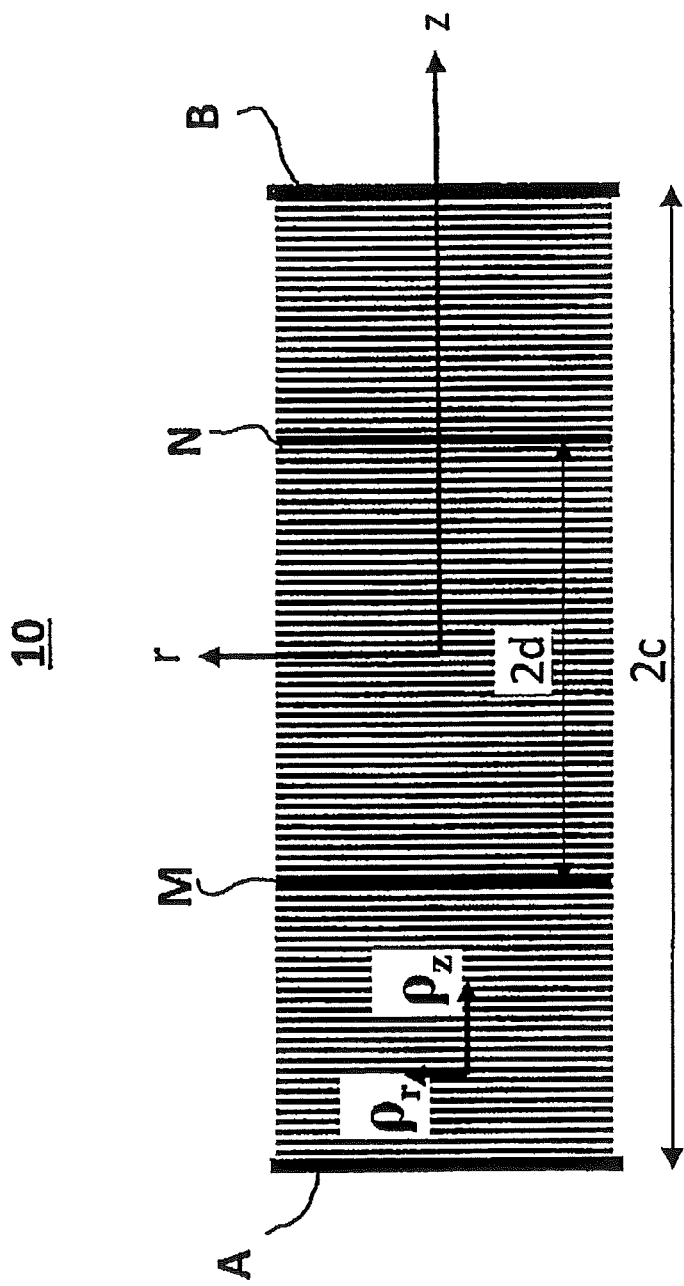
FIG. 1 is a side view of a cylindrical layered sample in a conventional four-electrode array.

FIG. 1 is a side view of a core sample 10 in a conventional four electrode array configuration. In particular, shown are two cap electrodes A and B, and two ring electrodes M and N. Cap electrodes A and B are adapted to be maintained in contact with respective first and second ends of a substantially cylindrical rock sample, while ring electrodes M and N are adapted to circumferentially contact the cylindrical sidewall of the sample at first and second locations along the length of the sample. Preferably, ring electrodes M and N are symmetrically located with respect to end cap electrodes A and B a distance 2d units apart, where the sample is 2c units long.

In accordance with one embodiment of the invention, the conventional four-electrode array of FIG. 1 is utilized for the purposes of measuring resistive anisotropy of a sample, as shall hereinafter be described. Specifically, there are two measurement modes utilized in accordance with the disclosed embodiment.

Figure 2:
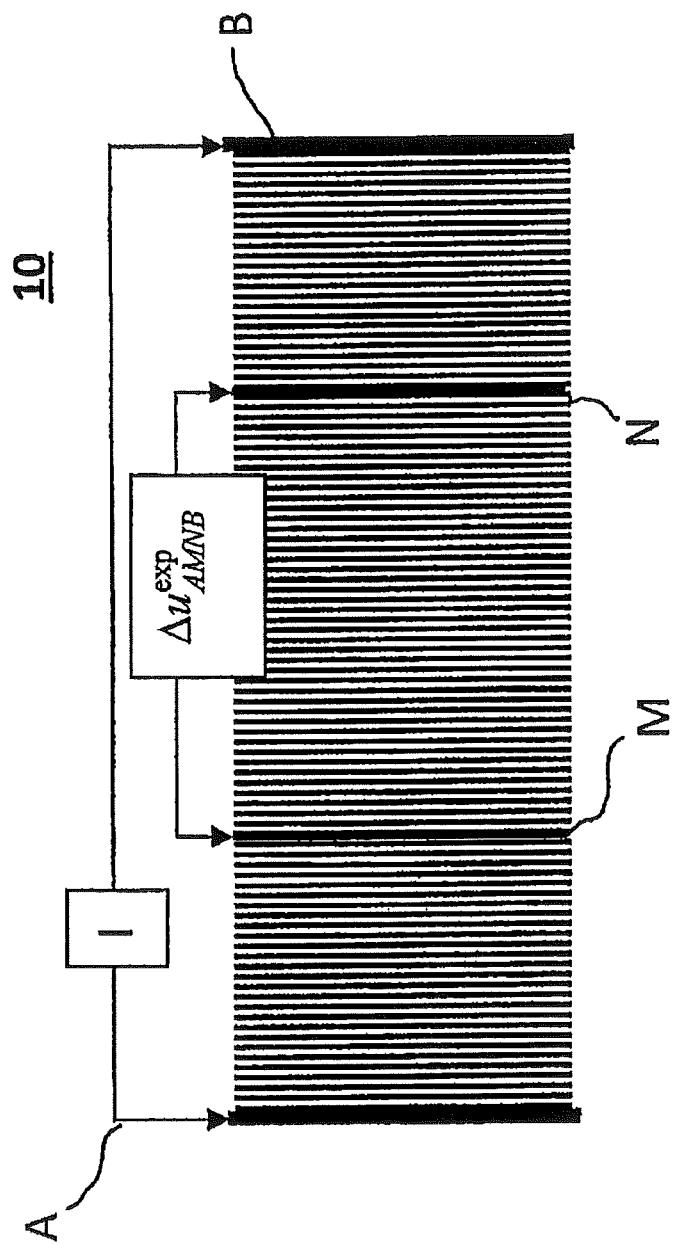
FIG. 2 is a side view of the sample from FIG. 1 schematically showing a first measurement mode configuration.

A first measurement mode is depicted in FIG. 2. In this measurement mode, current I is injected through cap electrodes A, B, and ring electrodes M, N are used to measure a difference in potentials $\Delta u_{AMNB}^{exp}$.

Figure 3:
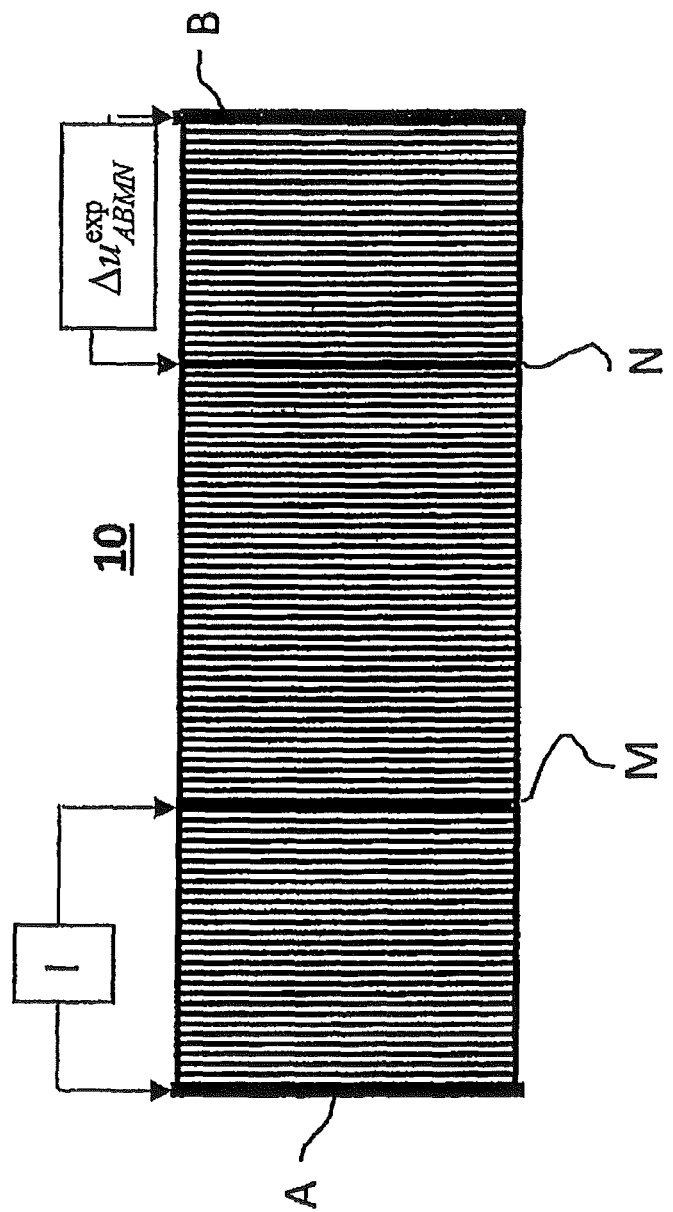
FIG. 3 is a side view of the sample from FIG. 1 schematically showing a second measurement mode configuration.

A second measurement mode is depicted in FIG. 3. In this measurement mode, current I is injected through cap electrode A and ring electrode M. Ring electrode N and cap electrode B are used to measure a difference in potentials $\Delta u_{ABMN}^{exp}$.

In this case of Measurement Mode 1 depicted in FIG. 2, the electric field E created by cap electrodes is homogeneous; the current I is uniformly distributed over the cylinder, and the current density vector has the only component $j_z$. According to these physical principles, we can write out the equations for the $E_z$ component of the electric field and for the registered signal $\Delta u_{AMNB}$:

$$E_z \approx -\frac{I\rho_z}{\pi a^2}\tag{2}$$

$$\Delta u_{AMNB} = \frac{I\rho_z}{\pi a^2}2d\tag{3}$$

In the case of Measurement Mode 2 depicted in FIG. 3, first consider the basic problem of distribution of the electric field potential in electrically anisotropic, conducting round cylinder.

Figure 4:
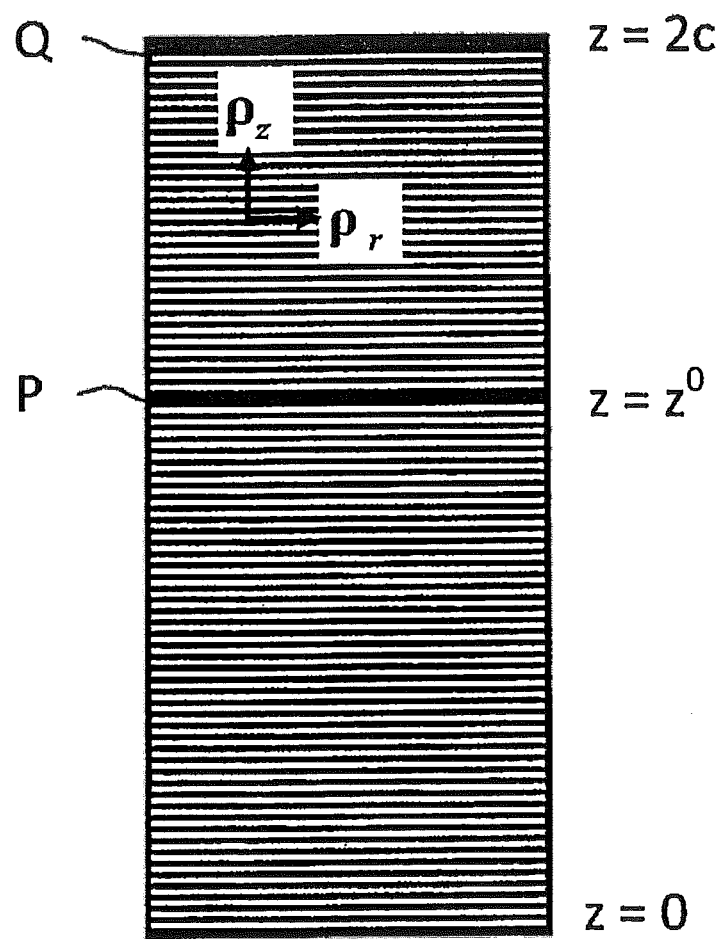
FIG. 4 is a side view of the sample from FIG. 1 showing axial dimensions and locations of electrodes thereon.

As indicated in FIG. 1, the height of the sample cylinder is 2c, the radius is a, the longitudinal and transverse resistivity are $\rho_z$ and $\rho_r$, respectively. Referring to FIG. 4, the electric current I in Measurement Mode 2 is supplied to the cylinder by means of electrodes P, Q of different shapes:

P: ring electrode located in $z^0$ and having the form of a thin belt tightly wrapped around the cylinder 10;

Q: one of the cap electrodes of the radius a pressed to the ends of the cylinder in z=0, z=2c. In the case under consideration, the current cap electrode is located in z=2c.

It should be noted that the presence of dead electrode (z=0) is taken into account when formulating the boundary problem for the potential.

It is first necessary to look for the following form of a solution to the formulated problem of the potential u:

$$u = u^0 + u^a,\tag{4}$$

where $$u^0 = -\frac{I\rho_z}{\pi a^2} \cdot z \cdot C.\tag{5}$$

The unknown constant C is to be determined, and function $u^a$ satisfies the following homogeneous conditions at the ends of the cylinder:

$$u^a|_{z=0} = u^a|_{z=2c} = 0.\tag{6}$$

To construct the solution, let us continue, in the odd manner, the function $u^a$, the field sources, and the cylinder onto the domain z<0.

As a result, the following initial equations are obtained to determine the constant C:

$$\int_{S|_{z=0}} j_z dS = 0 \text{ or } \int_{S|_{z=2c-0}} j_z dS = I \quad (7)$$

Taking into account equation (4), equations (7) may be rewritten as follows:

$$\int_{S|_{z=0}} j_z^a dS + I \cdot C = 0 \text{ or } \int_{S|_{z=2c}} j_z^a dS + I \cdot C = I \quad (8)$$

After the odd transform onto the domain z<0, the plane of the cylinder (z=0) becomes the plane of the zero potential. Therefore, let us present the solution for the potential $u^a$ as follows:

$$u^a = \sum_{n=1}^{\infty} A_n I_0(a_n r) \sin(a_n \Lambda z) \quad (9)$$

The boundary conditions (6) will be satisfied if $$a_n = \frac{\pi n}{2\Lambda c} \quad (10)$$

Now it is necessary to find unknown constants $A_n$. To this end, use the obvious relationships between the potential u, component of the electric field $E_r$, and current density $j_r$:

$$\frac{\partial u}{\partial r} = -E_r, \quad j_r = -\sigma_r \frac{\partial u}{\partial r}. \quad (11)$$

The equations for current density $j_r$ are as follows:

$$j_r = -\sigma_r \sum_{n=1}^{\infty} A_n a_n I_1(a_n r) \sin(a_n \Lambda z) \quad (12)$$

To find $A_n$, in equation (12) for $j_r$, assume r=a, multiply both sides of the equation by $\sin(a_p \Lambda z)$ and integrate from −2c to 2c. After transformations, the following equation for $A_n$ is applied:

$$A_n = \frac{I\rho_r}{\pi a \cdot 2c} \cdot \frac{\sin(a_n \Lambda z^0)}{a_n I_1(a_n a)}. \quad (13)$$

As a result, the following representation for $u^a$ is applied:

$$u^a(r, z) = \frac{I\rho_r}{\pi a \cdot 2c} \sum_{n=1}^{\infty} \frac{I_0(a_n r)}{a_n I_1(a_n a)} \sin(a_n \Lambda z^0) \sin(a_n \Lambda z). \quad (14)$$

For the purposes of the present disclosure, the following notations are used:

$$\tilde{z} = \frac{\Lambda z}{a}, \quad a_n a = p_n = n\frac{\pi a}{2\Lambda c}, \quad \delta p_n = \frac{\pi a}{2\Lambda c} \quad (15)$$

such that the above representation for the function $u^a$ can be rewritten as follows:

$$u^a(r, z) = \frac{I\rho_z}{\pi a^2} \cdot \frac{a}{\pi \Lambda} \cdot \delta p_n \cdot \sum_{n=1}^{\infty} \frac{I_0(p_n r/a)}{p_n I_1(p_n)} \sin(p_n \tilde{z}^0) \sin(p_n \tilde{z}). \quad (16)$$

Using (11)-(13), the expression for the constant C is:

$$C = 1 - \frac{z^0}{2c} \quad (17)$$

and the final equation for the potential on the surface of the cylinder (r=a) is:

$$u(z, z^0) = \quad (18)$$

$$-\frac{I\rho_z}{\pi a^2} \cdot z \cdot \left(1 - \frac{z^0}{2c}\right) + \frac{I\rho_z}{\pi a^2} \cdot \frac{1}{2c} \cdot \frac{a^2}{\Lambda^2} \cdot \sum_{n=1}^{\infty} \frac{I_0(p_n)}{p_n I_1(p_n)} \sin(p_n \tilde{z}^0) \sin(p_n \tilde{z}).$$

Considering a special case of the solution (18), let the ring electrodes be located symmetrically with respect to the center of the cylinder, at a distance of 2d from each other (see FIG. 1). Because in this case the distance between the cap electrodes AB=2c, the following equation for the signal $\Delta u_{ABMN}$, registered by this setup, is derived:

$$\Delta u_{ABMN} = \quad (19)$$

$$\frac{I\rho_z}{\pi a^2} \left[ -\frac{(c-d)^2}{2c} + \frac{a^2}{2\Lambda^2 c} \sum_{n=1}^{\infty} \frac{I_0(p_n)}{p_n I_1(p_n)} \sin\left(p_n \frac{\Lambda(c-d)}{a}\right) \sin\left(p_n \frac{\Lambda(c+d)}{a}\right) \right]$$

Resolution of the Setup with Cap and Ring Electrodes

In order to quantitatively describe the ability of the arbitrary measured function U(p) to resolve variations in parameter p, it is convenient to use a sensitivity function. The sensitivity $\eta_p$ of the function U(p) to the parameter p is defined as follows:

$$\eta_p = \left| \frac{\partial \ln|U(p)|}{\partial \ln|p|} \right|. \quad (20)$$

Figure 5:
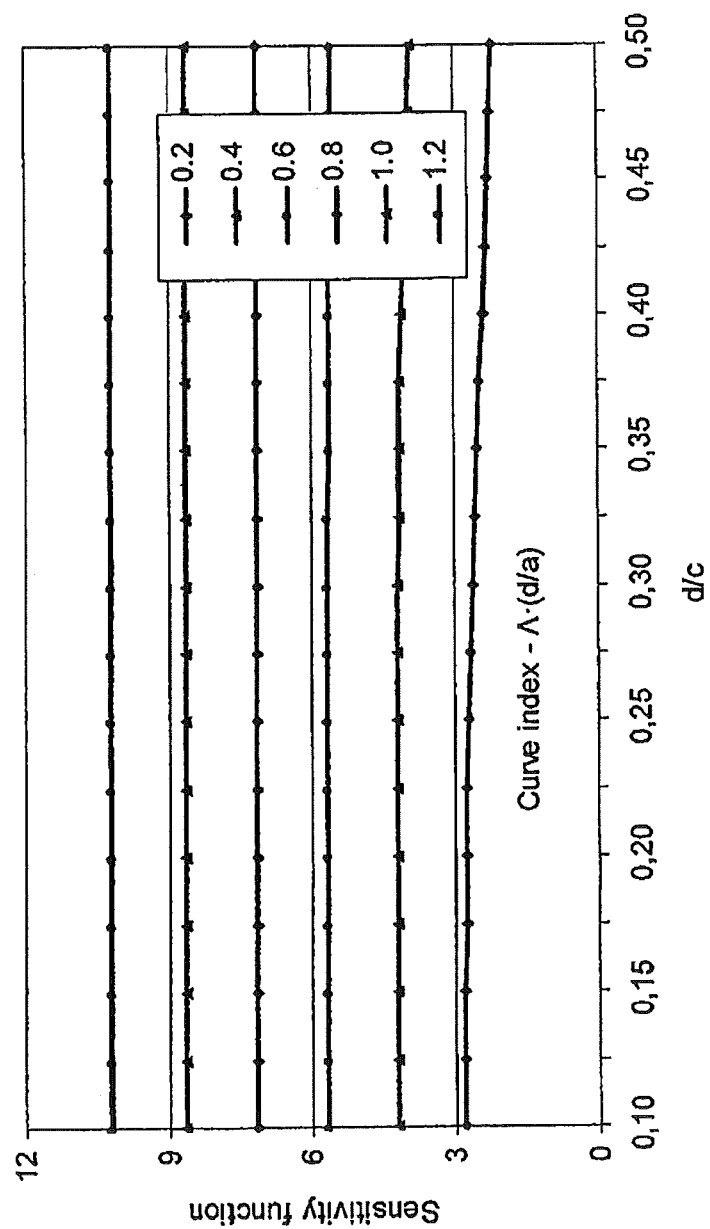
FIG. 5 consists of plots of the sensitivity functions U of an interpretation parameter to an anisotropy parameter.

Now consider the feasibility of four-electrode measurement configuration with cap and ring electrodes to evaluate the anisotropy parameter Λ (FIG. 1). In FIG. 5, the sensitivity curves for the interpretation parameter U are presented:

$$U = \frac{\Delta u_{ABMN}}{\Delta u_{AMNB}} \quad (21)$$

Here $\Delta u_{AMNB}$, $\Delta u_{ABMN}$ are signals of the configurations shown in FIGS. 2 and 3, respectively.

In FIG. 5 the values of the function describing sensitivity of the interpretation parameter U to the anisotropy parameter Λ are plotted. As follows from the data presented, sensitivity of the function U to the anisotropy parameter is high: basically, in all cases of interest $$\frac{\Lambda d}{a} \gtrsim 0.5 - 0.6$$

the function $\eta_\Lambda > 5$ and weakly depends on d/c.

It is well known to those of ordinary skill in the art that the optimal measuring system is characterized not only by high sensitivity of measured signal to the parameters of the medium under study, but also by a high signal-to-noise ratio. Consider the value of the signal $\Delta u_{AMNB}$ for a cylindrical core with a diameter of $\sim 4 \cdot 10^{-2}$ m and length of $\sim 7 \cdot 10^{-2}$ m. Suppose that the distance 2d between the ring electrodes be $\sim 2 \cdot 10^{-2}$ m. Then, for $I \sim 2 \cdot 10^{-3}$ A, $\rho_z \sim 10$ Ohm·m as it follows from (3), $\Delta u_{AMNB} \sim 0.3$ V.

Figure 6:
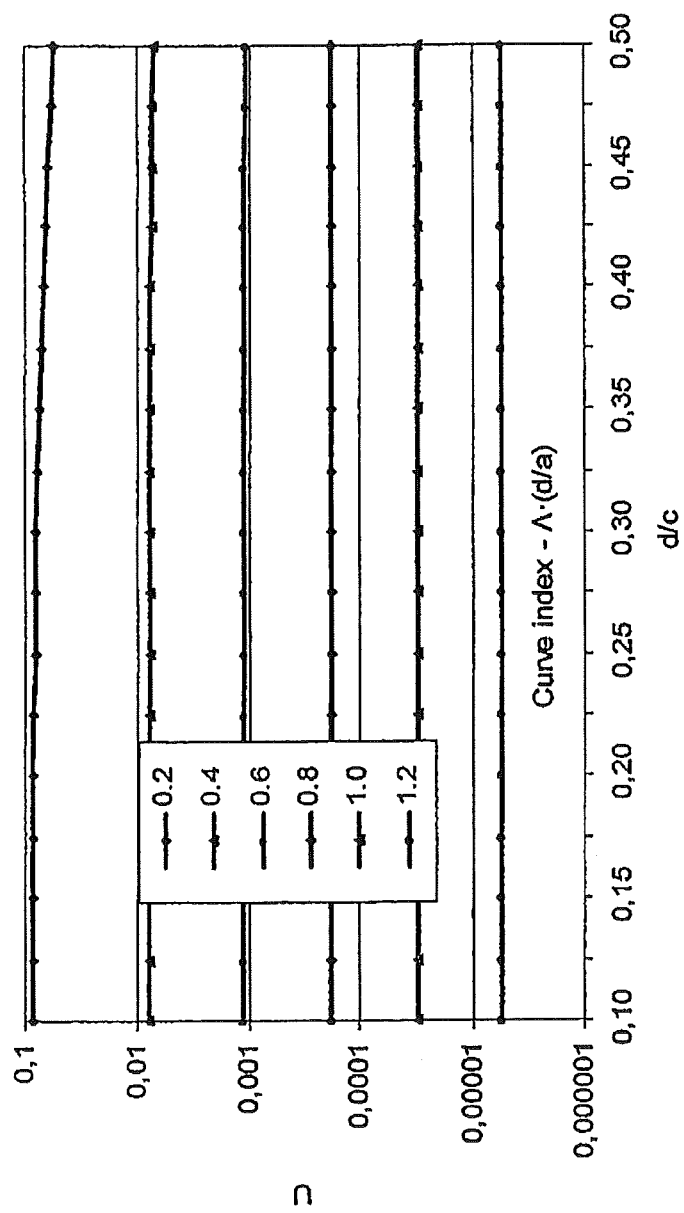
FIG. 6 consists of plots of the interpretation parameter U versus geometric parameter d/c.

Referring to FIG. 6, the parameter $U = \Delta u_{ABMN} / \Delta u_{AMNB}$ is plotted. As follows from the data presented, signals $\Delta u_{ABMN}$, are much smaller than $\Delta u_{AMNB}$ and basically do not depend on the parameter d/c.

Now assume that it is feasible to experimentally measure the difference in potentials $\sim 10^{-5}$ V. Then, for the case described above, it is possible to evaluate the anisotropy coefficient in those cores whose parameter $\Lambda \cdot (d/a) < \sim 1$, i.e. $\Lambda < \sim 2$. It should be noted that the possible anisotropy coefficient range widens with the increase in the core diameter.

Thus, joint analysis of sensitivity and the signals in the system under consideration leads to the following conclusion:

The feasibility of evaluating Λ through measurements of $\Delta u_{ABMN}$, $\Delta u_{AMNB}$ is determined mostly by an equipment potentiality to measure weak signals $\Delta u_{ABMN}$ accurately.

Together with sensitivity of the interpretation parameter to the anisotropy coefficient, it may be reasonable to consider distortions of the signal due to errors in measurement of electrode coordinates.

Figure 7:
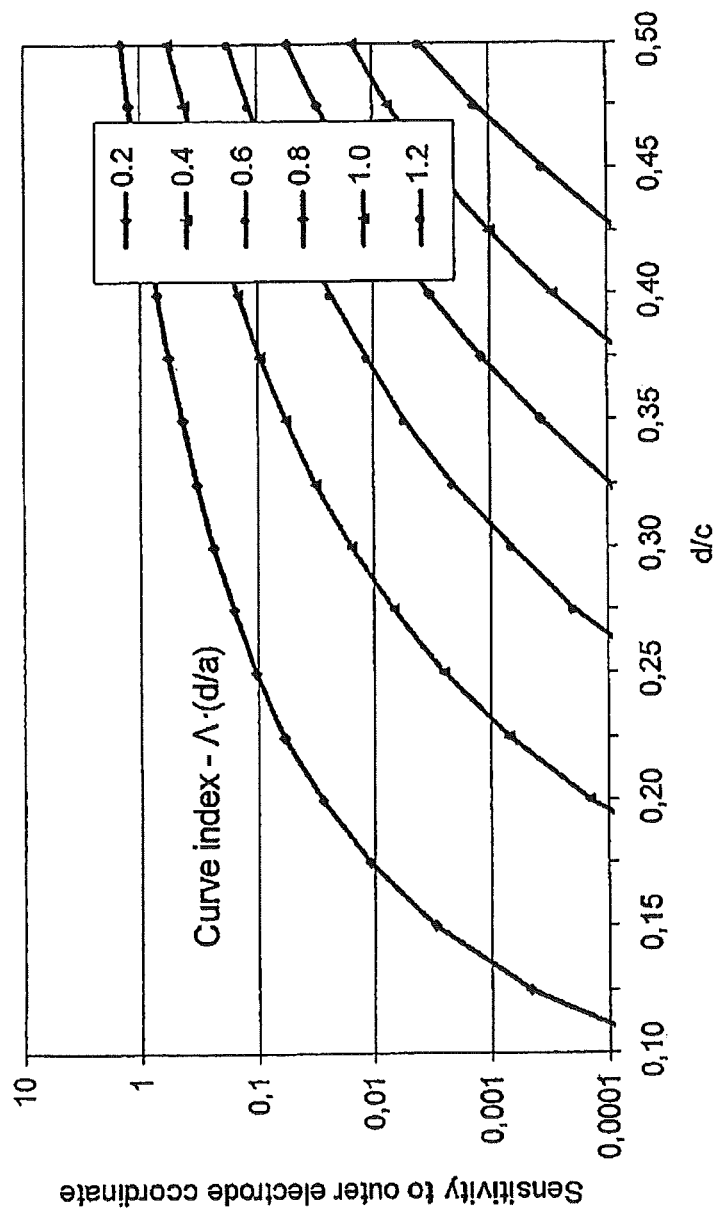
FIG. 7 consists of plots showing the sensitivity of the interpretation parameter U to the coordinate of the external electrode.
Figure 8:
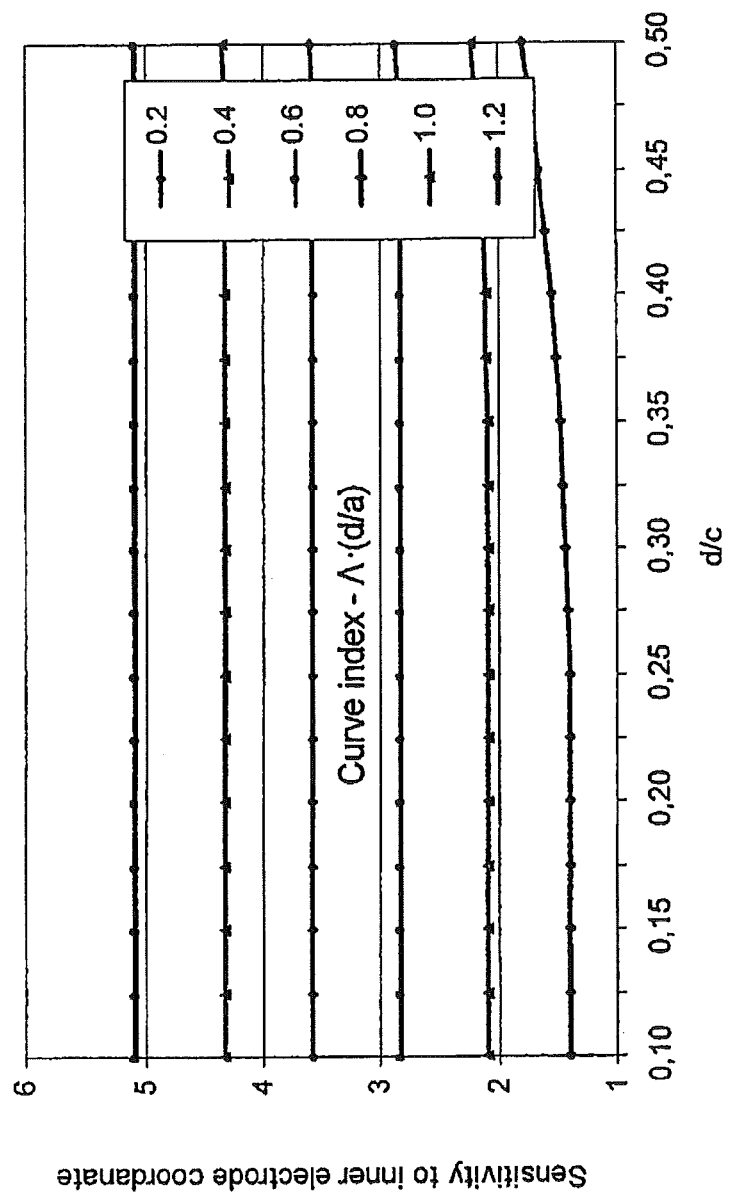
FIG. 8 consists of plots of the sensitivity parameter U to the coordinate of the internal electrode.

In FIGS. 7 and 8 the values of the functions describing sensitivity of the interpretation parameter U to coordinates of any external and internal electrode, respectively, are plotted.

As follows from the data presented in FIG. 7, sensitivity of U is much weaker to coordinate of any external electrode than to the anisotropy parameter. This beneficial difference increases dramatically with the increase of the anisotropy coefficient.

Sensitivity of the interpretation parameter U to coordinate of any internal electrode is essentially different (FIG. 8): sensitivity is weaker to coordinate of any internal electrode than to the anisotropy parameter for $\Lambda \cdot (d/a) > \sim 0.3$ and (d/c) $< \sim 0.5$ and it drops down by half for $\Lambda \cdot (d.a) > \sim 0.6$.

Figure 9:
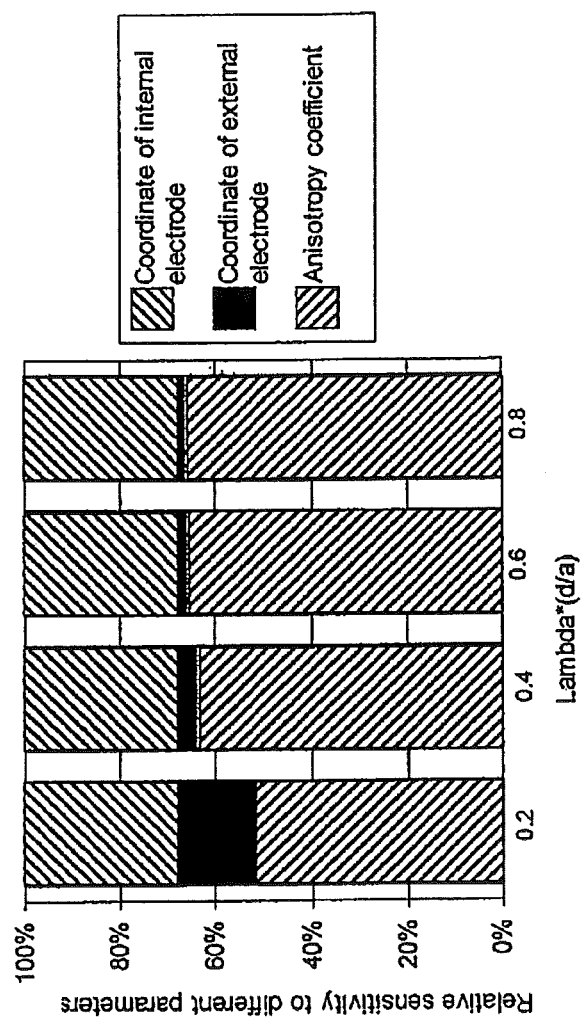
FIG. 9 graphs the relative sensitivity of the interpretation parameter U to coordinates of internal and external electrodes as well as to the anisotropy coefficient $\Lambda$ for the sample.

In FIG. 9, relative sensitivities to the anisotropy coefficient and coordinates of the external and internal electrodes is presented for (d/c)=0.4 (the sum of all relative sensitivities is 100%).

The following comment should be made. When electrodes are placed on the core surface, we do not measure coordinates of single electrodes, but rather distances between them. In this case the total error when fixing relative distances c/a and d/a is double that of the error in fixing relative distances z/a.

Thus, for $\Lambda \cdot (d/a) > \sim 0.6$ the relative error in the anisotropy parameter Λ is basically equal to the relative measurement error for relative distances c/a and d/a.

Algorithm for Finding the Anisotropy Coefficient Λ

Figure 11:
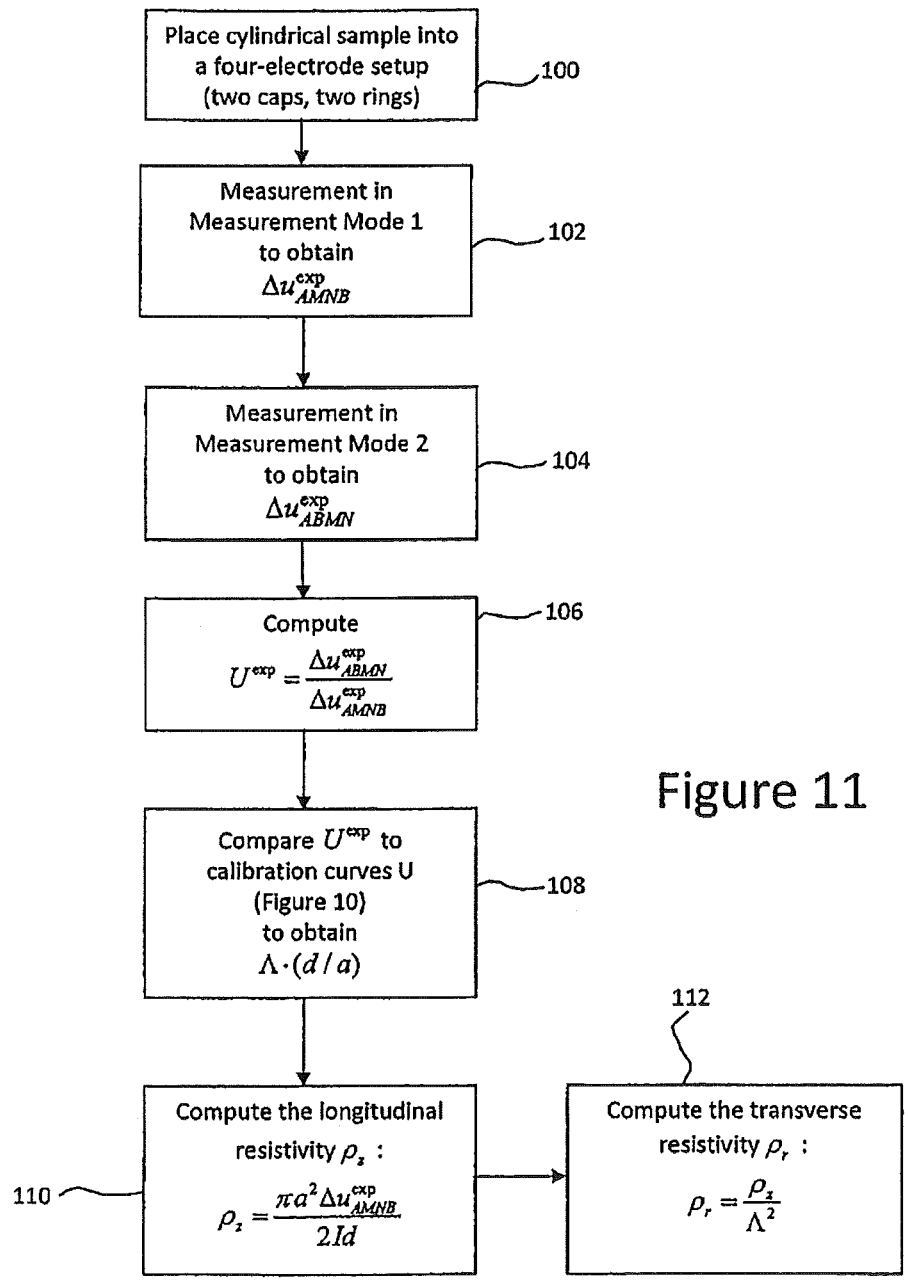
FIG. 11 is a functional flow diagram of a method of computing the transverse resistivity of a layered sample in accordance with one embodiment of the invention.

Referring to FIG. 11, there is shown a flow diagram illustrating one implementation in accordance with the present invention for finding the anisotropy parameter Λ for an anisotropic sample.

First, in step 100, a specially prepared cylindrical sample of the radius a and length 2c is placed into a four-electrode setup. Next, in steps 102 and 104, measurements of the difference in potentials for two modes of supplying the electric current I to the sample are performed, first Measurement Mode 1 (FIG. 2) in block 102, and then Measurement Mode 2, in block 104:

Measurement Mode #1 (FIG. 2):
  current I is injected through cap electrodes A,B
  ring electrodes M, N are used to measure the difference in potentials $\Delta u_{AMNB}^{exp}$ Measurement Mode #2 (FIG. 3):
  current I is injected through cap electrode A and ring electrode M
  ring electrode N and cap electrode B are used to measure the difference in potentials $\Delta u_{ABMN}^{exp}$ With the measurements from steps 102 and 104 available, the next step, in block 106, is to compute the experimental value of the function $$U^{exp} = \frac{\Delta u_{ABMN}^{exp}}{\Delta u_{AMNB}^{exp}}$$

Figure 10:
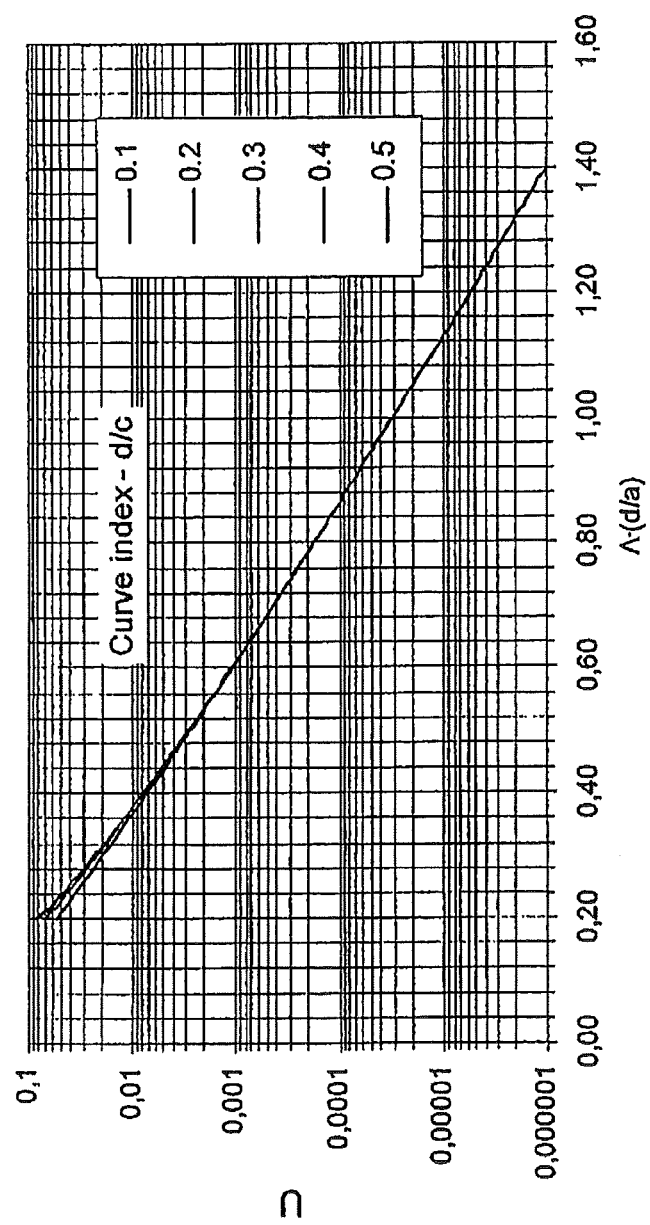
FIG. 10 consists of calibration curves for the evaluation of the anisotropy coefficient $\Lambda$ of the sample.

Next, as represented by block 108 in FIG. 11, it is necessary to solve the one-parameter inverse problem for the given value of d/c, i.e., comparing the experimental value of the function $U^{exp}$ with one of the calibration curves U shown in FIG. 10. The value of the parameter $\Lambda \cdot (d/a)$ where the experimental and theoretical values of the function U coincide most closely within a given error bars, (for example, where the values coincide within a predetermined error range), is the solution to the problem of finding the anisotropy coefficient Λ (values of geometrical characteristics d and a are known).

Next, in block 110, the longitudinal resistivity $\rho_z$ is computed according to:

$$\rho_z = \frac{\pi a^2 \Delta u_{AMNB}^{exp}}{2 I d}.$$

Finally, in block 112, transverse resistivity $\rho_r$ is calculated from known values of the anisotropy coefficient Λ and longitudinal resistivity $\rho_z$:

$$\rho_r = \frac{\rho_z}{\Lambda^2}$$

As described herein, the method in accordance with the presently disclosed embodiment of the invention involves several computational steps. As would be apparent by persons of ordinary skill, these steps may be performed by computational means such as a computer, or may be performed manually by an analyst, or by some combination thereof. As an example, where the disclosed embodiment calls for a comparison of theoretical and experimental values of a variable function, it would be apparent to those of ordinary skill in the art that such comparison could be performed based upon a subjective assessment by an analyst or by computational assessment by a computer system properly programmed to perform such a function. To the extent that the present invention is implemented utilizing computer equipment to perform one or more functions, it is believed that programming computer equipment to perform these steps would be a matter of routine engineering to persons of ordinary skill in the art having the benefit of the present disclosure.

From the foregoing disclosure, it should be apparent that a method and apparatus for assessing resistive anisotropy of a rock sample by indirect measurement of the longitudinal and transverse resistivity of the sample has been disclosed. It should also be apparent that the present invention may be practiced utilizing a conventional four-electrode measurement setup.

Although a specific embodiment of the invention as well as possible variants and alternatives thereof have been described and/or suggested herein, it is to be understood that the present disclosure is intended to teach, suggest, and illustrate various features and aspects of the invention, but is not intended to be limiting with respect to the scope of the invention, as defined exclusively in and by the claims, which follow.

Indeed, it is contemplated and to be explicitly understood that various substitutions, alterations, and/or modifications, including but not limited to any such implementation variants and options as may have been specifically noted or suggested herein, including inclusion of technological enhancements to any particular method step or system component discovered or developed subsequent to the date of this disclosure, may be made to the disclosed embodiment of the invention without necessarily departing from the technical and legal scope of the invention as defined in the following claims.

What is claimed is:

1. A method of evaluating an earth formation, comprising obtaining a sample of said formation;
   contacting a first and second electrodes to opposing ends of said sample;
   contacting third and fourth electrode to said sample at points intermediate to said opposing ends;
   measuring a first potential difference between said first and second electrodes while injecting current into said sample through said third and fourth electrodes;
   measuring a second potential difference between said first and third electrodes while injecting current into said sample through said second and fourth electrodes; and
   deriving first and second resistivity values for said sample as a function of said first and second potential differences.

2. The method of claim 1, wherein said first resistivity value is longitudinal resistivity of said formation, and said second resistivity value is transverse resistivity of said formation.

3. The method of claim 2, wherein said step of deriving first and second resistivity values comprises:
   deriving an anisotropy coefficient for said formation as a function of said first and second resistivity values.

4. The method of claim 3, wherein deriving the anisotropy coefficient comprises:
   comparing a function of said first and second resistivity values with precomputed calibration curves to obtain said anisotropy coefficient.

5. The method of claim 4, wherein said precomputed calibration curves are computed as a function of theoretical values of said first and second potential differences.

6. The method of claim 5, wherein said sample is substantially cylindrical.

7. The method of claim 6, wherein said third and fourth electrodes comprise ring electrodes extending substantially around said sample.

* * * * *